US006864378B2

(12) United States Patent
Bhatia

(10) Patent No.: US 6,864,378 B2
(45) Date of Patent: *Mar. 8, 2005

(54) INTEGRATED CONTINUOUS PROCESS FOR ANHYDRO SUGAR ALCOHOL MANUFACTURE

(75) Inventor: Kamlesh Kumar Bhatia, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/414,607

(22) Filed: Apr. 16, 2003

(65) Prior Publication Data

US 2004/0110994 A1 Jun. 10, 2004

Related U.S. Application Data

(60) Provisional application No. 60/373,214, filed on Apr. 17, 2002.

(51) Int. Cl.[7] .............................................. C07D 493/04
(52) U.S. Cl. ....................................................... 549/464
(58) Field of Search ............................................ 549/464

(56) References Cited

U.S. PATENT DOCUMENTS

| 4,506,086 A | 3/1985 | Salzburg et al. |
| 4,564,692 A | 1/1986 | Feldmann et al. |
| 4,861,513 A | 8/1989 | Lueders et al. |
| 5,306,831 A | 4/1994 | Beshouri et al. |

FOREIGN PATENT DOCUMENTS

| WO | WO 00/14081 | 3/2000 |
| WO | WO 01/92246 | 12/2001 |

*Primary Examiner*—Bernard Dentz

(57) ABSTRACT

An integrated continuous process is disclosed for the manufacture of high purity, polymer grade dianhydro sugar alcohols, such as isosorbide, by the dehydration of corresponding sugar alcohols. The water vapors evolved during the dehydration are used to separate product dianhydro sugar alcohols from the high boiling byproducts in the reaction mass. The product is recovered from the vapor stream as high purity crystals. The high boiling reaction byproducts are recycled.

20 Claims, 1 Drawing Sheet

INTEGRATED CONTINUOUS PROCESS FOR ANHYDRO SUGAR ALCOHOL MANUFACTURE

This application claims priority from Provisional Application Ser. No. 60/373,214 filed Apr. 7, 2002.

FIELD OF THE INVENTION

This invention concerns an integrated, continuous process for the manufacture of high purity, polymer grade dianhydro sugar alcohols, such as isosorbide, by the dehydration of the corresponding sugar alcohols, using the water evolved to separate the product as vapors and recovering the product from the vapor stream as high purity crystals. The high boiling byproducts of the dehydration reaction are recycled.

TECHNICAL BACKGROUND OF THE INVENTION

Anhydro sugar alcohols, in particular derivatives of mannitol, iditol, and sorbitol, are known for their therapeutic uses and uses in food. At least one of these, isosorbide, 1,4:3,6-dianhydrosorbitol, is useful as a monomer used in the manufacture of polymers and copolymers, especially polyester polymers and copolymers.

Anhydro sugar alcohols are produced by dehydration of the corresponding sugar alcohols (or monoanhydro sugar alcohols) by the action of various dehydration catalysts, typically strong acid catalysts. Examples of these catalysts include sulfonated polystyrenes ($H^+$ form) and various mineral acids, such as HCl, $H_3PO_4$, HF and $H_2SO_4$.

Batch processes for the preparation of dianhydro sugar alcohols by acid dehydration have been described in the prior art.

In particular, a batch process for the formation of the dianhydro sugar alcohol isosorbide has been described as a two-step process involving intramolecular dehydration of sorbitol to sorbitan (1,4-monoanhydrosorbitol), and further reaction of sorbitan to isosorbide (1,4:3,6-dianhydrosorbitol) in an acid catalyzed dehydration-cyclization. In this process, an aqueous solution of sorbitol is charged to a batch reactor. The temperature is increased to 130° C.–135° C. under vacuum (35 mm Hg) to remove the water. When the sorbitol melt is free of water, a catalyst, usually sulfuric acid, is added and the temperature and vacuum levels are maintained. The operable temperature range of the reaction is very narrow. Higher temperatures lead to decomposition and charring of the end product, while lower temperatures inhibit the reaction rate due to difficulties in removal of the water of reaction. This reaction produces isosorbide and a higher molecular weight byproduct. The byproduct is presumably produced by water elimination between two or more sorbitol molecules, but its exact nature is not clearly defined. See G. Flèche and M. Huchette, *Starch/Starke* (1986), 38(c), 26–30 and Roland Beck, Pharm. Mfg Inc. (1996), 97–100. Other monoanhydro byproducts, 2,5-anhydro-L-iditol and 2,5-anhydro-D-mannitol, are also known to be produced under some reaction conditions (*Acta. Chem. Scand.* B 35, 441–449 (1981)).

For isosorbide to be used as a monomer in high volume polymers and copolymers, for applications such as containers, it needs to be produced in large quantities, preferably in a continuous process.

WO 00/14081 describes a continuous process for producing anhydro sugar alcohols, especially isosorbide, comprising the steps of introducing at least one sugar alcohol or monoanhydro sugar alcohol into a reaction vessel; dehydrating the sugar alcohol or monoanhydro sugar alcohol in the presence of an acid catalyst and an organic solvent to form a reaction product which is at least partly soluble in the organic solvent; removing water from the reaction vessel; removing organic solvent comprising the dissolved reaction product from the reaction vessel; separating the reaction product from the removed organic solvent; and recycling the organic solvent into the reaction vessel. The large amounts of organic solvent required for such a process make it economically and environmentally undesirable.

U.S. Pat. No. 6,407,266 describes a continuous process in which a process stream containing at least one sugar alcohol or monoanhydro sugar alcohol and, optionally, water is introduced to the first stage of a multistage reactor and then intimately contacted with a countercurrent flow of an inert gas at elevated temperature. This inert gas removes the bulk of any water present in the process stream. This dewatered process stream is then intimately contacted with a dehydration catalyst, with a counter current flow of an inert gas at elevated temperatures to remove water of reaction as formed. Finally, the product is removed from the bottom of the reactor.

The reaction product obtained by processes such as the above, contains about 70 to 80% by weight isosorbide and 20 to 30% undesired reaction byproducts. The reaction product thus needs to be subjected to one or more separation steps, such as evaporation, distillation or chromatographic separation, to isolate the isosorbide. Chromatographic separation is disclosed in U.S. Patent Application No. 60/246038 (filed 6, Nov. 2000). Separation by vaporization or distillation is difficult because of the low vapor pressure of isosorbide. For example, we have found that at 140° C., the vapor pressure is only 1.75 mm Hg. Evaporation or distillation at temperatures not much higher than about 140° C. is desirable to-minimize product degradation and obtain good purity isosorbide, but the recovery is poor. At higher temperatures, e.g., 170° C., more isosorbide is recovered, but it is of poorer quality.

U.S. Pat. No. 4,564,692 discloses a process using crystallization from aqueous solutions:to obtain the high purity needed for applications as polyol components in polyester and polyurethane polymers.

Commonly owned U.S. application Ser. No. 10/414,611, filed simultaneously herewith, discloses a combined reaction-separation process wherein dianhydro sugar alcohols are obtained as vapors in a stream of water vapor. The vapor streams from such a process are condensed, and the isosorbide needs further purification to obtain the high level of purity required for use in polymers such as polyesters, that is, at least 99.8% pure.

Commonly owned U.S. application Ser. No. 10/414,606, filed simultaneously herewith, provides an effective means of recovering and purifying dianhydro sugar alcohols from aqueous vapor strams, wherein purification by crystallization occurs while recovering the product by condensation, and a separate crystallization step is eliminated.

Commonly owned U.S. application Ser. No. 10/414,605, filed simultaneously herewith, provides a process wherein the reaction byproducts and dianhydro sugar alcohols not recovered initially from the reaction mass are recycled back to the reaction step and overall yield of the dianhydro sugar alcohols, such as isosorbide, is increased.

There is a need for an effective, integrated process to conduct the dehydration reaction and separation in a single, multistage reaction vessel; recover the product directly from the vapor stream as purified crystals; and recycle reaction byproducts so as to increase overall process yield. The object of the present invention is to provide such an effective, integrated process suitable for continuous, large-scale production of high purity, polymer grade dianhydro sugar alcohols in high yield.

SUMMARY OF THE INVENTION

In accordance with the objectives of the present invention, there is provided an integrated process for continuous production of high purity, polymer grade dianhydro sugar alcohol, comprising the steps of:
a) continuously feeding an aqueous solution of a sugar alcohol to a reaction vessel maintained at an elevated reaction temperature and a reduced pressure;
b) contacting the sugar alcohol with a dehydration catalyst;
c) evaporating most of the water from the aqueous solution;
d) continuously dehydrating the sugar alcohol, with the evolution of water vapor, to form a reaction mass comprising dianhydro sugar alcohol, monoanhydro sugar alcohols, dimers and polymers;
e) separating from the reaction mass most of the dianhydro sugar alcohol formed, by volatilizing it with the water vapor evolved to form a vapor stream and a byproduct stream, comprising monoanhydro sugar alcohol; isomers, dimers, polymers, and the dianhydro sugar alcohols not volatilized form the reaction mass;
f) withdrawing the vapor stream comprising dianhydro sugar alcohol and water from the reaction vessel, and partially condensing the stream under controlled temperature and pressure to recover most of the dianhydro sugar alcohol as a slurry of dianhydro sugar alcohol crystals in a mother liquor;
g) separating the dianhydro sugar alcohol crystals from the mother liquor;
h) withdrawing from the reaction vessel the byproduct stream, comprising monoanhydro sugar alcohol isomers, dimers, polymers, and the dianhydro sugar alcohols not volatilized from the reaction mass in (e);
i) diluting the byproduct stream with water and allowing most of the polymers to precipitate;
j) separating the precipitated polymers to form a solution of soluble sugar alcohol species; and
k) recycling the solution of soluble species to the reaction vessel; while maintaining the flows in and out of steps (a)–(k) at substantially steady rates and substantially steady-state processing conditions.

The reaction is preferably conducted in a multistage vessel. The anhydro sugar alcohol and byproducts recycle stream is fed to the bottom-most stage. The reaction product is carried from the bottom to the next stage above along with the evolved water vapor. The high boiling byproducts are removed as a liquid stream from the topmost stage.

Optionally, the dianhydro sugar alcohol vapor evolved is purified by contacting with liquid isosorbide generated by internal reflux or with an external reflux of a concentrated solution, such as the mother liquor which has been separated from the crystals.

The product crystals can also be further purified. For example, they may be dissolved in water and the solution treated with a suitable adsorbent, such as activated carbon, to remove any remaining color forming impurities.

DETAILED DESCRIPTION OF THE INVENTION

Figure 1:
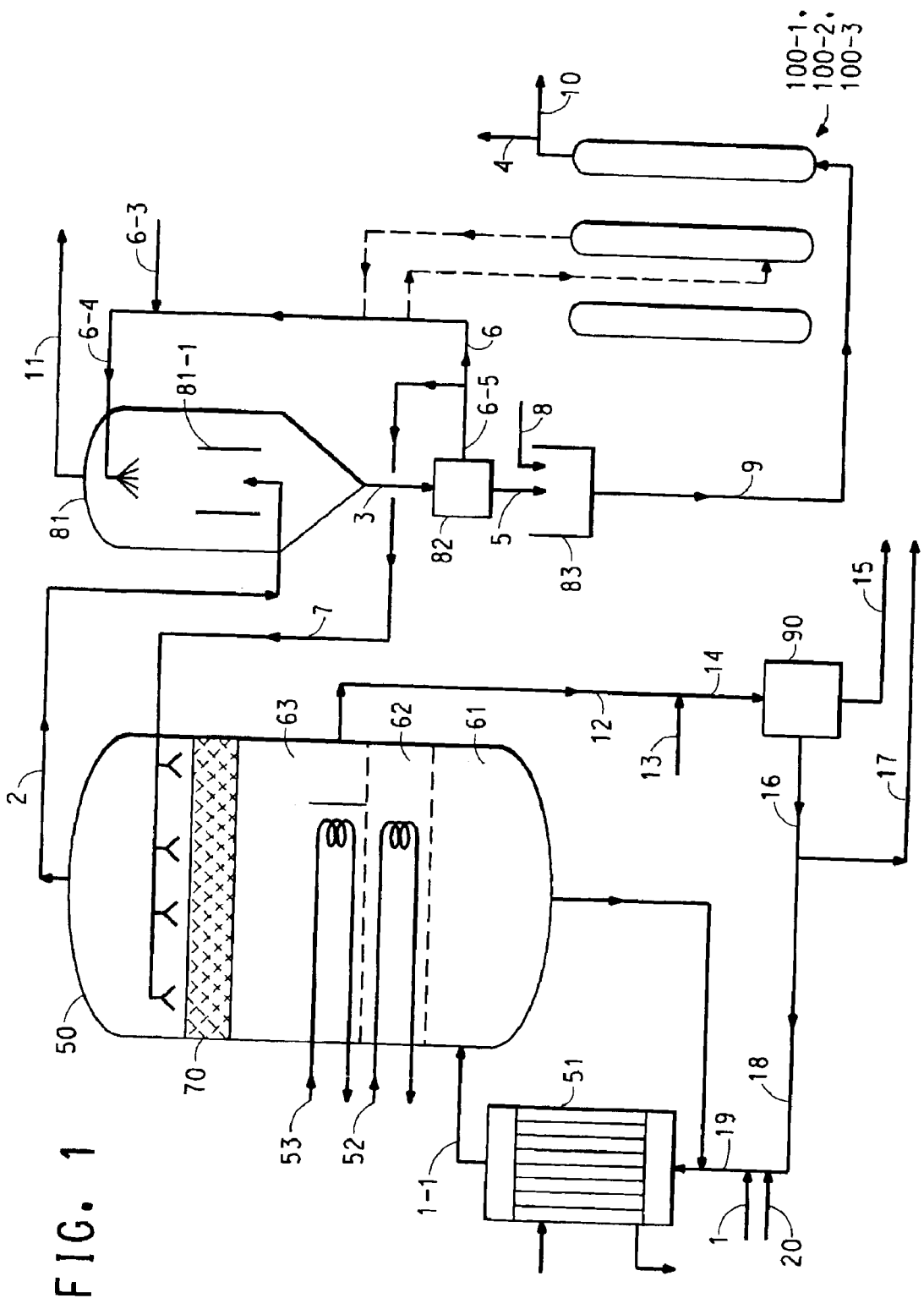
FIG. 1 is a schematic representation of an embodiment of the process of the present invention.

The present invention discloses a high yield, economical and environmentally benign process to manufacture high purity dianhydro sugar alcohols, in an integrated processing unit.

Dehydration of Sugar Alcohols and Their Separation. In the process of the present invention, the dehydration reaction that produces the dianhydro sugar alcohol and the separation of the product from the reaction mass are carried out at the same time. This is achieved by continuously feeding to the reaction vessel an aqueous solution of sugar alcohol and using the evolved water vapor to mix, agitate the reaction mass, and assist in removing the dianhydro sugar alcohol formed. The reaction vessel is preferably compartmentalized into two or more stages, such that the reaction occurs as if it were being done in a number of well-mixed reactors in series. This reduces the residence time required to complete the reaction, and the reaction mass is not subjected to long periods at elevated temperature. Furthermore, the reaction mass is transported from one stage to the next by the water vapor itself.

The process of this invention thus generally includes the steps of introducing an aqueous solution of a sugar alcohol, preferably at about 40%–70% concentration by weight, to a multistage reaction vessel; evaporating most of the water from this aqueous solution; dehydrating the sugar alcohol in the presence of a catalyst to form anhydro sugar alcohol and evolve additional water vapor; and removing the anhydro sugar alcohol product along with the water vapor from the top of the reactor. The process is continuous in that the steps of introducing the sugar alcohol, removing the product vapor stream, and removing the high boiling byproducts occur simultaneously, and their rates are coordinated to maintain a steady amount of reaction mass in the reactor.

The reaction vessel may be maintained at the desired elevated temperature by any suitable means, such as including internal heating coils in each stage or circulating the reaction mass through an external heat exchanger. Separate heat input for each stage allows temperature control at each stage and operation at an optimum temperature profile. An external heat exchanger is preferred for the first stage for ease of fabrication, particularly at large scale, to handle the large heat load required for evaporating most of the excess water at that stage.

Typical sugar alcohols, including tetritols, pentitols and hexitols, are suitable for use in the process as starting materials. The starting materials may be sugar alcohols, monoanhydro sugar alcohols, or a mixture thereof. Particularly preferred starting materials include erythritol, threitol, xylitol, arabinitol, ribitol, glucitol (also known as D-sorbitol or sorbitol), D-mannitol (mannitol), galactitol and iditol. The use of sorbitol is most preferred because sorbitol is readily available and can be obtained on a large industrial scale by the reduction of glucose with hydrogen, and the dehydration product, isosorbide, is especially valuable for use in the preparation of polyester polymers and copolymers. The preferred form of sorbitol is as an aqueous solution, about 45% to 70 wt %.

The catalysts used to facilitate the dehydration reaction are typically strong acid catalysts. Soluble acid catalysts such as sulfuric acid, phosphoric acid, p-toluene sulfonic acid, methanesulfonic acid and the like may be used. Sulfuric acid is a preferred soluble catalyst.

Acid anion exchange resins may also be used, such as sulfonated polystyrenes, for example, AG50W-X12

(BioRad) or perfluorinated ion-exchange polymers, such as Nafion® (E. I. du Pont de Nemours and Company, Wilmington, Del.). Inorganic ion exchange materials may also be used, such as acidic zeolites. In particular, H-beta zeolite from Degussa (Frankfurt, Germany) may be used in the process disclosed herein.

For the present invention, a soluble catalyst is preferred, and sulfuric acid is most preferred. In this most preferred mode, the sulfuric acid comprises 0.25 wt % to 2.5 wt % of the reaction mass, preferably 0.5 wt % to 1.5 wt %. The sulfuric acid is supplied to the reactor as an aqueous solution ranging from 10% to 97% sulfuric acid. The acid strength and the manner of injection should be such that there is minimal detrimental byproduct formation at the point of introduction. The acid catalyst can be injected along with the sugar alcohol feed stream or directly into the reaction vessel at the first stage. In the integrated process of the present invention, most of the acid catalyst gets recycled with the high boiling byproduct stream. It is necessary to add only a small make-up quantity of the acid catalyst. This is preferably injected into the recycle stream.

The dehydration is performed at elevated temperatures between 100 and 180° C., preferably at temperatures between 115° C. and 160° C., and most preferably at temperatures between 120° C. and 145° C. The elevated temperature of the dehydration reaction promotes rapid dehydration of the starting materials. However, overtemperature or prolonged high-temperature operation promotes the formation of byproducts and the further conversion of the desired product to undesired secondary products over time. Therefore, it is desirable to remove the desired reaction product from the high temperature reaction mixture rapidly to protect it against further reaction or decomposition. In the process of the present invention, the product is removed from the reaction mass as it is formed, along with the water vapor evolved.

The dehydration is preferably performed under reduced pressure for effective removal of water and for volatilizing the product formed from the reaction mass. The pressure depends upon the reaction temperature, moles of water vapor available per mole of product, and the desired degree of product separation. For volatilizing most of the product formed, the pressure is generally 10 to 60 mm Hg, preferably 10 to 50 mm Hg, most preferably 15 to 25 mm Hg.

The vapors leaving the reaction mass are generally about 98% pure dianhydro sugar alcohols along with the water vapor evolved through evaporation of the free water and the dehydration reaction. The vapor stream may contain 20 to 30% by weight dianhydro sugar alcohols, the balance being mostly water vapor. These are withdrawn from the top of the reaction vessel under the reduced pressure, leaving behind the high boiling byproducts and unvolatilized portion of the dianhydro sugar alcohol that are withdrawn from the reactor as a liquid.

In a preferred embodiment of the process of the present invention, the purity of the dianhydro sugar alcohols in the vapor stream obtained as described above is enhanced within the reaction vessel before withdrawing it from the reactor. This is achieved by contacting the vapors with a liquid stream of dianhydro sugar alcohols. The liquid stream can be generated internally by cooling the vapors or injected from outside. Through this treatment, the purity of the dianhydro sugar alcohols can be enhanced to greater than 99%. The vapor stream is then withdrawn from the top of the reactor for recovery and further purification of the dianhydro sugar alcohol.

Recycle of High Boiling Reaction Byproducts. The high boiling liquid stream withdrawn from the reactor is treated and recycled back to the reactor so as to capture most of the unvolatilized dianhydro sugar alcohols contained therein, thereby increasing the overall yield of the process. The basis and details of this treatment and recycle are described below.

The dehydration reaction of sugar alcohols to dianhydro sugar alcohols is believed to proceed in two steps: (1) dehydration of the sugar alcohols to monoanhydro sugar alcohols with the evolution of one mole of water for every mole of sugar alcohol, followed by (2) dehydration of the monoanhydro sugar alcohols to dianhydro sugar alcohols with the evolution of a second mole of water. The dehydration reaction is, however, accompanied by several side reactions that lead to generation of unwanted byproducts For example, in the dehydration of sorbitol to isosorbide, sorbitol first dehydrates to the various sorbitan isomers, namely 1,4-anhydro-D-glucitol (also known as 1,4-sorbitan); 3,6-anhydro-D-glucitol; 2,5-anhydro-D-mannitol; and 2,5-anhydro-L-iditol. The 1,4 and 3,6 isomers dehydrate further to form isosorbide; the 2,5 isomers do not. Furthermore, as the dehydration reaction proceeds, various species present in the reaction mass, including sorbitol, the four monoanhydro isomers, and isosorbide, react with each other to form a number of different dimers, which then polymerize to form higher oligomers. The dehydration-derived oligomers have been referred to in the prior art, and are referred to herein, as "polymer." In addition, the various species present undergo a host of other side reactions, which generate color forming species, charred material, and various decomposition products.

The byproducts thus formed, comprising mostly the undesired monoanhydro sugar alcohols (e.g., the 2,5-sorbitan isomers), dimers, and polymer, may constitute, at the completion of the dehydration reaction, about 20 to 30 weight % of the reaction mass, depending upon the reaction conditions. A yield loss of about 20 to 30% to byproducts is typical for the conversion of sorbitol to isosorbide at a reaction temperature of about 140° C. in the presence of sulfuric acid catalyst.

The sorbitans, dimers, and polymer byproducts are all considerably higher boiling than isosorbide. For example, the vapor pressure of the sorbitans is only about 0.04 mm Hg at 140° C., about one-fiftieth that of isosorbide. The dimers are even less volatile, and the polymers are practically nonvolatile. Therefore, the water vapor volatilizes most of the dianhydro sugar alcohols but not such high boiling byproducts. However, under the simultaneous reaction-separation conditions, about 20 to 30% of the product dianhydro sugar alcohols such as isosorbide also remain unvolatilized along with the high boilers. Similar behavior may be expected for products derived from other sugar alcohols.

The stream containing the high boilers is diluted with water to cool the stream and dilute the acid catalyst. Upon sufficient dilubon and cooling, most of the polymeric species precipitate from the solution. The polymers are then separated from the solution via a suitable solid-liquid separation device, such as a filter, and the solution containing the dissolved monoanhydro sugar alcohols, dimers, and dianhydro sugar alcohol, is recycled back to the reaction vessel. A small portion of this stream may be purged to circumvent build up of certain minor, not completely identified, water-soluble byproducts in the reaction mass.

The recycle solution may be injected into the reaction vessel as a separate stream or as a mixture with fresh sugar alcohol feed added. If a soluble acid catalyst is used, most of it also gets recycled back to the reactor, and catalyst consumption is thereby reduced considerably. Any acid catalyst lost in the process, for example, through a purge as described above, can be made up by injecting make-up acid into the recycle stream.

As the byproducts are recycled back to the reactor, their concentration will start to build up in the reaction mass. This causes their rate of consumption to form polymer to increase. After some time, or several recycles, the process reaches a steady state, i.e., the byproduct concentration remains constant, as the rate of newly formed byproduct species and dimers equals the rate of their disappearance to form polymer.

Thus, the byproduct recycle process in the process of the present invention accomplishes removal of most of the byproducts formed in the dehydration reaction as washed polymer, and recycles the dianhydro sugar alcohol that otherwise would be lost with the high-boiling byproducts.

As described above, recycle of byproducts leads to higher concentration of byproducts in the reaction mass. Consequently, the dehydration reaction takes place under dilute conditions, i.e., lower concentration of the reacting species. Thus, the rate of dimer formation is reduced relative to the rate of formation of dianhydro sugar alcohol product. This results in a higher reaction yield of the desired product. The process of the present invention allows this advantage of conducting the reaction under dilute conditions without introducing any new solvents into the reaction system and makes use of the reaction byproducts themselves to serve as a diluent.

Product Recovery and Purification. The vapor stream produced in the present invention is generally a stream of 98–99% purity dianhydro sugar alcohol, along with water vapor evolved through reaction and evaporation, as described above. Such streams may contain 20–30% by weight dianhydro sugar alcohol product, the balance being water vapor. Dianhydro sugar alcohols, isosorbide in particular, can be recovered from such vapor streams and concurrently purified by only partially condensing the vapor stream under controlled temperature and reduced pressure. Under these conditions, almost all of the dianhydro sugar alcohol is condensed, but most of the water remains in the vapor state. Furthermore, the condensate is a supersaturated solution that forms dianhydro sugar alcohol crystals of high purity, leaving behind in solution the more polar impurities, such as the monoanhydro sugar alcohols and the very small amount of color-forming species volatilized from the reaction mass. The recovery and purification process thus provides an improved process wherein condensation and subsequent vaporization of all the water is unnecessary, and a separate crystallization step is eliminated.

Appropriate choice of the condensation temperature allows control of the degree of supersaturation so as to obtain an optimum balance of nucleation and crystal growth rates, crystals to mother liquor ratio, and product purity desired for a particular application. The appropriate balance can be determined experimentally within the temperature range that gives supersaturated condensate. Generally, a temperature at the high end of the range is preferred for ease of cooling, lower solution viscosity, and speed of crystallization. A higher degree of supersaturation gives faster nucleation and crystal growth rates, but the purity of the crystals may suffer if crystal growth is too fast. Under 14 mm pressure, the preferred temperature range is about 33° C. to about 48° C., most preferably from 37° C. to 45° C. for isosorbide.

The optimum condensation temperature range can be varied by changing the condensation pressure. Lower pressures give a wider temperature range and higher degree of supersaturation but may require refrigeration to condense the water vapor leaving the condensation/crystallization vessel. For isosorbide, at about 9 mm Hg, the temperature range may be from 20 to 55° C., preferably between 25 and 50° C. Higher pressures are advantageous for subsequent water condensation but result in a narrower temperature range for product recovery and crystallization. Under higher pressures, more water gets condensed during the partial condensation and the solution is less supersaturated. Generally, the partial condensation pressure for recovery and crystallization is from about 5 to 30 mm Hg, preferably from 10 to 20 mm Hg, and most preferably from 12 to 18 mm Hg.

The purification and recovery steps of the present invention are conducted continuously, such that:
 (a) the vapor stream of water and dianhydro sugar alcohols is fed continuously to a condensation vessel maintained at the preferred temperature and pressure;
 (b) the stream is allowed to continuously condense most of the dianhydro sugar alcohols as a supersaturated solution and precipitate crystals, to produce a slurry of dianhydro sugar alcohol crystals in a supersaturated solution;
 (c) the slurry of (b) is continuously withdrawn from the vessel;
 (d) the uncondensed vapors, mostly water, are continuously withdrawn from the vessel to maintain the desired pressure;
 (e) the vapors from (d) are continuously condensed in a secondary condenser connected to a vacuum source to withdraw any noncondensibles in the feed and air leaking into the processing stream; and
 (f) the crystals from the slurry of (c) are continuously separated from the solution, and the mother liquor is recycled back to the condensation/crystallization vessel.

The crystals may be separated from the solution by means known in the art, such as filtration and centrifugation. For best purity, the product cake is preferably washed to displace the mother liquor. Since anhydro sugar alcohols are highly soluble in water, it is preferred that very cold, demineralized water, or, more preferably, a solution of purified dianhydro sugar alcohols be used for the washing.

All or a portion of the mother liquor may be purged to remove impurities, such as color-forming moieties, from the system and to maintain those at a low level in the slurry. The amount of purge depends upon the purity of crystals desired for a particular application. Higher purge results in a lower level of impurities in the slurry and higher purity crystals. The purged mother liquor may be treated to remove the impurities and recycled to the condensation/crystallization vessel or used in applications for which purity is not very critical. All or a portion of the mother liquor may also be subjected to fractional crystallization to recover more crystals before it is recycled, if the somewhat lower purity crystals thus obtained are suitable for a desired use.

In one embodiment of the process of the present invention, the condensate obtained by partial condensation of the vapor stream is withdrawn from the condensation vessel as a concentrated solution and allowed to crystallize in a separate crystallizer or subjected to fractional crystallization. This may be useful for obtaining a higher concentration of solids in the slurry and reducing the liquid load on the solid liquid device. Allowing the crystallization to occur in the condensation vessel itself is preferred for economic reasons, as it eliminates the need for a separate crystallizer.

Partial condensation for the process of the present invention may be conducted in a condensation device of any design known in the art. A preferred device is a direct contact condenser wherein the vapors to be condensed are intimately contacted with a cooling liquid. Such direct contact may be achieved by bubbling the vapor through the liquid or by spraying the liquid into the vapor, or by flowing the liquid as films in the vapor, or by employing a combination of such means.

The heat evolved in condensation and crystallization may be removed by any heat exchange means known in the art. A preferred method, particularly for large-scale operation, is to circulate the liquid through a heat exchanger external to the condensation vessel. The liquid in the case of partial condensation of dianhydro sugar alcohols would be the condensate itself, preferably the mother liquor.

In a preferred embodiment of the recovery and purification process of the present invention, heat removal required for condensation and crystallization is achieved by simply injecting fresh water into the vessel to contact with the vapors. Under the reduced pressure and the operating temperature of the vessel, this excess water gets evaporated using the heat of the process fluid. This preferred means of cooling eliminates the need for an external recirculation exchanger. It also improves process reliability by eliminating cooling the mother liquor, a concentrated solution from which dianhydro sugar alcohols may crystallize and deposit on exchanger tubes at unfavorable velocities. It is preferred that the water used for cooling has been purified, and preferably demineralized, so external impurities are not introduced into the system when a highly pure product is desired. The water may be introduced directly into the condensation vessel, for example, as a spray, or injected into the recycled mother liquor stream or a circulating condensate/slurry stream, or a combination of the above.

In a preferred condenser-crystallizer design particularly suited for large scale production, all or a part of the vapor stream is sparged into the condensate, i.e., the slurry phase, most preferably under one or more draft tubes. The vapor bubbles rising though the draft tubes provide intimate contact, circulate the slurry up and around, and keep the crystals in suspension for uniform growth. The vessel thereby behaves like a draft tube crystallizer without the need for an internal circulation/suspension impeller, and high concentrations of crystals can be maintained to reduce the liquid load on the solid-liquid (i.e., crystals-mother liquor) separation device. The solids concentration in the slurry is generally 10–30% by weight, preferably 15–25% by weight.

The product crystals separated and washed as described above may be purified further if desired. For example, they may be dissolved in water and the solution treated with a suitable adsorbent, such as activated carbon, to remove any remaining color forming impurities.

In certain applications, it may be desirable to obtain the dianhydro sugar alcohol in the form of a slurry or a solution in a liquid other than water, such as a glycol when the isosorbide is to be incorporated into a polyester. For example, when isosorbide is to be incorporated into polyethylene terephthalate, it may be desirable to provide the isosorbide as a solution in ethylene glycol. Such a solution may be prepared by dissolving the purified isosorbide crystals in ethylene glycol.

For such cases, it may be preferable to employ an embodiment of the partial condensation and crystallization process, wherein the crystallization is conducted in a fluid other than water.

In this embodiment of the process, the vapor stream comprising dianhydro sugar alcohol and water is contacted with a colder stream of a solvent, that may or may not contain water, to cool the vapors below the melting point of dianhydro sugar alcohols (62° C. in the case of isosorbide). The solvent is a liquid in which the dianhydro sugar alcohol is only partially soluble below its melting point. At such a temperature and under reduced pressure, most of the dianhydro sugar alcohol is condensed, but only very little water.

The solvent is preferably a high boiling liquid, so only a negligible amount is vaporized and lost with the water vapor. For purification by crystallization to be effective, it is preferred that the solvent also be a polar liquid in which the more polar monoanhydro sugar alcohols and other impurities formed in the reaction step, such as color-forming bodies, are more soluble than the dianhydro sugar alcohol. Examples of such high-boiling solvents are linear glycols such as ethylene glycol and propylene glycol. These are particularly suitable if the end-use involves incorporating the dianhydro sugar alcohol product into polyesters. For example, if it is desired to incorporate isosorbide into polyethylene terephthalate, ethylene glycol would be the preferred solvent.

The total quantity of fresh solvent introduced into the process for this purpose is controlled in relation to the dianhydro sugars to be less than that quantity which could completely solubilize the dianhydro sugar alcohols. The condensate is then a supersaturated solution from which the dianhydro sugar alcohol precipitates as purified crystals. The quantity of fresh solvent is regulated to obtain a slurry of crystals that can be handled easily. The slurry is withdrawn from the condenser-crystallizer vessel. The purified crystals are separated from the slurry by means such as filtration and centrifugation, and the mother liquor is recycled back to the vessel for contacting with the vapor. To maintain the desired condensation temperature, the heat produced from cooling the vapor, condensing the dianhydro sugar alcohol, and crystallizing them must be removed. This can be accomplished by introducing a chilled stream of fresh solvent, cooling the slurry with an internal or external recirculation heat exchanger, cooling the recycle mother liquor or simply introducing cooling water (either separately or along with the fresh solvent or with the recycle mother liquor) and removing the heat through evaporation of this water under the operating conditions of the condenser-crystallizer. The process is preferably conducted continuously so that the vessel's input and output streams are regulated at a substantially constant rate and are coordinated so as to maintain a steady reduced pressure and a steady slurry level in the vessel.

When the dianhydro sugar alcohol is isosorbide and the solvent is ethylene glycol, the operating temperature for the embodiment of the process described above may be from about 20° C. to 57° C. The solubility of isosorbide in ethylene glycol at these temperatures ranges from about 60 to about 93% by weight. A preferred temperature range is 25° C. to 50° C., with the corresponding isosorbide solubility about 65 to about 87% by weight. The operating pressure may be from 5 mm Hg to about 50 mm Hg, preferably 10 to 30 mm Hg. Generally, a higher temperature and lower pressure are preferred so as not to condense much water from the vapor stream. The vapor pressure of ethylene glycol in the above preferred temperature range is less than 1 mm Hg; thus, very little of it is vaporized into the water vapor. The small amount of ethylene glycol contaminating the water stream maybe removed before disposing of the water stream, e.g., by feeding it to a glycol-water separation column.

The purified isosorbide crystals recovered from the process may be dissolved in a terephthalic acid slurry preparation tank or redissolved in ethylene glycol, either for use as a solution or for further purification treatment.

It will be obvious to one skilled in the art that the partial condensation method could also be advantageously practiced to recover most of the dianhydro sugar alcohol from a vapor stream as a concentrated solution if further purification is not needed for the intended use, or if a concentrated solution is desired for conducting purification by means other than the in situ simultaneous crystallization described here. Recovery by partial condensation would be advantageous in such cases, as it would eliminate the costs associated with condensing all of the vapor stream and then having to vaporize most of the condensed water in a subsequent step.

A preferred embodiment of the present invention for the production of anhydro sugar alcohols is described below in relation to FIG. 1. The operating conditions described are for the case when the starting material is sorbitol and the product is isosorbide. As shown in FIG. 1, the dehydration takes place in the reaction vessel (50), which is fitted with sieve plates (72 and 74) for multistage operation and equipped with heaters (51, 52, and 53). It is provided with supply lines for starting materials, such as the aqueous solution of sugar alcohol (1) and acid catalyst (20), as well as outlet lines for product vapor removal (2) and high boilers removal (12).

Any means of heating may be employed to maintain the reaction vessel at the desired temperature. Internal steam coils for heaters (52) and (53) for stages (62) and (63), respectively, are schematically illustrated in FIG. 1. For the first stage, where most of the heat must be supplied in order to evaporate most of the water, an external heat exchanger (51) is selected for ease of fabrication. This heater is preferably a steam, shell and tube, heat exchanger that circulates the reaction mass through it with thermosyphon action. This provides for effective heat transfer without a circulation pump. With such an external heater, the feed material and catalyst are supplied to the reactor via this heater via line (1—1) along with the byproduct recycle stream (18) and the recirculating stream.

In the process of the present invention, the dehydration reaction is preferably conducted in multiple stages. The number of stages is preferably at least 2 and more preferably 3 to 6. FIG. 1 illustrates the use of 3 stages, (61), (62), and (63), which are achieved with 2 sieve plates (72 and 74) as shown. The hole size and open area of the sieve trays are designed such that, at the vapor velocities for which the reactor is designed, the vapor stream can carry the reaction mass by entrainment through the sieve trays from one stage to the stage above with minimal leakage ("weeping") back to the stage below. The reaction vessel is designed for a vapor velocity that is high enough to provide good agitation and contact with the reaction mass, but low enough such that carry-over of reaction mass with the vapor stream leaving the reactor is insignificant. Generally, the velocity is such that the product of the vapor velocity in ft/sec times the square root of the vapor density in lbs/ft$^3$ is 0.2 to 1.5, preferably 0.5 to 1.0. The open area of the sieve trays may be 1 to 10% of the total area, preferably 3 to 5%, and the holes may be 1/16 to 3/8 inch in diameter, preferably 1/8 to 1/4 inch in diameter.

The reactor of FIG. 1 is sized and flow rates are adjusted such that hold up time for the isosorbide reaction mass is 1 to 5 hours, preferably 2 to 3 hours, with the assumption that reaction temperatures are 130° C. to 150° C. and catalyst (sulfuric acid) concentration in the reactor is about 0.5 to 2% by weight of the organics in the reaction mass. In one preferred embodiment of the process, a gradually increasing temperature profile is maintained for optimizing isosorbide generation rate and yield; the temperature is about 125° C. in the first stage (61), 135° C. in the second stage (62), and 145° C. in the third stage (63).

Most of the water is evaporated in the first stage (61) by means of the external circulation heater (51). The water vapors-carry the reaction mass to the second stage (62), where further dehydration takes place, and so on, to the third stage wherein the dehydration is essentially completed and most of the isosorbide generated gets transferred from the liquid reaction mass to the vapor phase. Under the reduced pressure of about 18 to 22 mm Hg and about 145° C. reaction temperature, the high boiling byproducts are not vaporized but are left as liquid in the third stage (63) and withdrawn via line (12).

Under the reaction conditions, the isosorbide product is about 50 times more volatile than the nearest high-boiling component. Thus, the non-water component of the vapors leaving the third stage is about 98% isosorbide. The purity may be enhanced to greater than 99% isosorbide by contacting the vapors with a small amount of liquid isosorbide. The liquid stream may be generated by condensing isosorbide internally from the vapors, using cooling coils, or injected from outside. A spray of isosorbide mother liquor is schematically shown, via line (7), in FIG. 1. The vapor-liquid contacting may be achieved using any appropriate device known in the art. Depicted schematically in FIG. 1 is a low pressure-drop (about 2 mm Hg) structural packing (70). The vapor stream containing mostly water and isosorbide is taken out of the reactor via line (2). The higher boiling reaction byproducts comprising undesired sorbitans, dimers, polymers, and isosorbide that is not vaporized with the water vapor are removed via line (12).

The higher boiling byproducts (12) are diluted with cooling water via line (13) in amount sufficient to precipitate most of the polymers from the solution. The quantity of water is at least equal to that of the high boilers (by weight). Preferably, the water added is about 2 lbs water/lb of high boilers. Addition of large quantities of water, however, is not necessary and not desirable as it increases the water load on the equipment.

Therefore, it is preferred that the water added is not greater than 4 lbs/lb of high boilers. The water may be mixed with the high boilers by, any means known in the art, for example, a stirred mixing vessel, an inline mixer, or simply a mixing tee. These are not explicitly shown in FIG. 1. Dilution of the high boilers with water at ambient temperature reduces the acid concentration and cools the high boilers. Under these conditions, the polymer present in the high boilers starts to precipitate.

Optionally, the acid concentration can be reduced by neutralizing it with a suitable base, preferably an inexpensive inorganic hydroxide that reacts with the acid to form an insoluble salt.

Another option is to let the diluted mixture cool further by heat loss to the atmosphere or, for ease in further handling, by cooling in a heat exchanger. These options can result in more complete precipitation of the polymer and reduce the water load and the load on further processing equipment.

The mixture of high-boilers and water is fed to a solid-liquid separation device (90), via line (14), where the precipitated solids, comprising mostly polymer, are separated. This can be any suitable device known in the art, such as a filter or a centrifuge. The filter cake obtained in these devices is preferably subjected to a wash cycle with cooling water to wash away the acid and byproduct solution from the filter cake. The washed filter cake, represented by line (15), is then removed from device (90) and disposed of in a suitable manner. The liquid part, comprising a solution of the remaining dissolved byproducts, such as the monoanhydro alcohols and dimers and the unrecovered dianhydro sugar alcohol, is removed via line (16) for recycle back to the reactor via line (18).

The recycle solution can be injected into the reaction vessel (50) as a separate stream or as a mixture with fresh sugar alcohol feed added. Most of the acid catalyst also gets recycled back to the reactor, and catalyst consumption is thereby reduced considerably. Any acid catalyst lost in the process, for example, through a purge such as via line (17) as described below or through the optional neutralization, if employed, can be made up by injecting make up acid via line (20).

The byproduct recycle in the process of the present invention accomplishes removal of most of the byproducts formed in the dehydration reaction, as washed polymer via line (15), and recycles the isosorbide that otherwise would be lost with the higher-boiling byproducts.

In the process of the present invention, a portion of the byproducts solution from line (16) may be purged via line (17) to circumvent buildup of certain minor, not completely identified, water-soluble byproducts, such as color-forming species, in the reaction mass. The stream may be treated further to recover useful species, depending upon economics, or disposed of in a safe manner.

The vapor stream leaving the reactor via line (2), comprising mostly dianhydro sugar alcohol, such as isosorbide, and water vapor, and minor amounts of impurities, such as monoanhydro sugar alcohols and color-forming species formed during the conversion of sugar alcohols to dianhydro sugar alcohols, is fed via line (2) to the condensation-crystallization vessel (81) and sparged under the draft tube (81-1). The vapor stream is partly condensed by contacting it with the colder condensate pool in the vessel and a spray, via line (6-4), of dianhydro sugar alcohol diluted with cooling water. The vapor stream is thereby cooled to the temperatures described earlier to condense virtually all of the dianhydro sugar alcohol as a supersaturated solution. This solution is allowed to form purified crystals in the vessel, resulting in a slurry. The uncondensed vapor, mostly water, is continuously withdrawn from the vessel via line (11) to maintain the vessel under a reduced pressure as described earlier. The slurry is circulated within the vessel up and around the draft tube with the rising vapor bubbles. The slurry is continuously withdrawn from the vessel via line (3), to maintain a substantially steady level in the vessel, and is conducted to centrifuge (82) to separate the product crystals. The product cake is washed in the centrifuge with a concentrated solution of purified dianhydro sugar alcohol, obtained, e.g., via line (4), and is discharged from the centrifuge (82) via line (5-1). The washed crystals are the purified dianhydro sugar alcohol product. It is conducted via line (5) for further treatment to suit the desired application. The mother liquor separated in the centrifuge is conducted via line (6-5) for recycle. A small portion of the mother liquor is used to provide liquid reflux in the reactor via line (7). Most of the mother liquor is recycled via line (6). It is diluted with cooling water, line (6-3), and sprayed in the vessel via line (6-4). The quantity of cooling water that enters the system via line (6-1) is controlled to maintain the condensation and crystallization vessel at the desired temperature.

In one embodiment of the process of the present invention the product crystals are purified further to remove any trace amounts of impurities, particularly the color-forming species. This is accomplished by treating a solution of the product with a suitable adsorbent, such as activated carbon. Referring to FIG. 1, the product crystals are dissolved with demineralized water, supplied via line (8), in mix tank (83). The solution is conducted via line (9) to an adsorption column packed with the suitable adsorbent. The solution is passed over the adsorbent and removed from the column as refined product solution via line (10). A portion of this solution may be made available, via line (4), as a wash liquor for washing the product cake in the centrifuge (82).

For uninterrupted continuous operation, it is preferred to use three adsorption columns (100-1, -2, -3). The product solution is passed through the first column, (100-1), and then switched to the second column, (100-2) before the breakthrough of impurities. At that time, the first column is used to treat the mother liquor by circulating a portion of the mother liquor from line (6) through the column. This maintains the impurities in the crystallization vessel (81) at low levels to yield crystals of desired purity. When the product solution is switched from the second column (100-2) to the third column (100-3), column (100-2) is used for treating the mother liquor, while the adsorbent in column (100-1) is regenerated for treating the product solution. In this manner, each of the three columns in turn treats product solution, treats mother liquor, and undergoes regeneration. Thus, uninterrupted product treatment is maintained.

For uses such as a monomer or comonomer for polyesters production, the refined product solution can be used as is, for example, in preparing a terephthalic acid slurry for esterification. Alternatively, it can be treated further as needed for a desired application. For production of polymers, it is preferred that the refined solution is passed through polishing filters to remove any suspended fine particles and meet desired optical purity specifications. Polishing filters of any design known in the art can be employed. Cartridge filters using a suitable filter medium are commonly employed in such applications.

The process of the present invention thus provides an integrated unit for continuously conducting dehydration of sugar alcohols to dianhydro sugar alcohols, separation of the product from the reaction mass, purification of the product, and refining the product for economical, large-scale manufacture of dianhydro sugar alcohols such as isosorbide.

EXAMPLE

Manufacture of Isosorbide at Nominal 18 Million lbs./Year

Referring to FIG. 1, reactor (50) is approximately 12 ft in diameter by 15 ft in height. It is equipped with sieve plates, heat exchangers, and structured packing.

The condensation-crystallization vessel (81) is 9 ft. in diameter by 12 ft. in height. It is equipped with draft tube (81-1) and spray nozzles.

A stream of 70% by weight sorbitol (balance water) is introduced via inlet (1) at a rate of 5460 lbs/hr. It contains 3833 lb or 21 lb-moles of sorbitol. Heat input to stage heaters (51), (52), and (53) is adjusted to maintain the temperatures at 125, 135, and 145° C., respectively. Pressure in the headspace above the third stage is maintained at about 18 to 20 mm Hg. The dehydration reaction through all the stages forms about 16.8 lb-moles of isosorbide (80% yield). 4.2 lb-moles of starting sorbitol go to byproducts comprising monoanhydro sorbitol derivatives, dimers, oligomeric and polymeric materials, and decomposition products. The total amount of water vapor produced from feed stream evaporation, evaporation of water in the recycle stream, and the dehydration of sorbitol is about 464 lb-moles/hr. Under steady state reaction conditions, about 78% of the isosorbide formed, plus that entering with the recycle stream, about 18.9 lb-moles/hr, volatilizes in 98% purity into the water vapor. The bottoms are removed via line (12) at a rate of about 3270 lbs/hr. Under these conditions, the hold up time is about 3 hours.

With recycle of the byproducts as described herein, the byproduct stream, line (12), reaches a steady state concentration. Under the steady continuous operating mode, it contains about 28% isosorbide, 58–60% sorbitan isomers, 10–12% water insoluble polymer, and about 1.4–1.5% by weight sulfuric acid and is removed via line (12) at a rate of 3270 lbs/hr. It is mixed with 6900 lbs/hr of water via line (13) and the insoluble polymer is allowed to precipitate. It is then fed via line (14) to a filter (90), wherein the precipitated polymer is removed, as a filter cake, at a rate of 370 lbs/hr of polymer, which is washed with part of the water from line (13) and discharged from line (15). The filtrate, containing about 920 lbs/hr isosorbide and 1930 lbs/hr water-soluble byproducts and 50 lbs/hr of the acid catalyst, is discharged via line (16) at a rate of about 9800 lbs/hr. About one-seventh of this stream is purged via line (17). The remainder, about 8400 lbs/hr stream, is supplemented with make up sulfuric acid at a rate of 7 lbs/hr, as a 50% solution, via line (20) and injected back to the reaction step via line (18) along with fresh sorbitol feed. Thus, it recycles about 790 lbs/hr isosorbide, 1654 lbs/hr byproducts, and most of the acid catalyst back to the reaction-separation part of the process. About 7 lbs/hr of acid catalyst is lost through the purge. This is made up by the fresh sulfuric acid feed, via line (20), at a rate of 7 lbs/hr, as a 50% solution, to maintain a steady catalyst concentration of about 0.75% by weight of the total organics (on a water-free basis) that enter the reaction system via line (19).

The vapors volatilized in the reactor are contacted via line (7) with about 480 lbs/hr of mother liquor from the crystallization step. After this contact, the vapor stream is greater than 99% pure isosorbide (water-free basis) and leaves the reactor via line (2). It is continuously fed to the condensation-crystallization vessel (81) via line (2) at a rate of 11,100 lbs/hr. It contains about 25% by weight isosorbide and feeds isosorbide to the vessel at a rate of 2760 lbs/hr. Most of the isosorbide is condensed from the stream by contacting it with the pool of slurry and the diluted recycle mother liquor via line (6-4) spray, as has been described. The isosorbide is allowed to crystallize in the vessel. The temperature of the slurry pool is controlled at about 39–42° C. by regulating the flow of fresh, demineralized water into the system via line (6-3) at about 1245 lbs/hr. The pressure in the vessel is maintained at 14–15 mm Hg by continuously withdrawing the water vapors from the vessel via line (11). Isosorbide slurry containing about 15% by weight isosorbide crystals is continuously withdrawn via line (3) from the vessel at a rate of 15,330 lbs/hr. The slurry is maintained at a steady level in the vessel near the top of the draft tube (81-1). The slurry stream comprises about 2300 lbs/hr isosorbide crystals and about 13,030 lbs/hr mother liquor. The mother liquor is about 95% by weight isosorbide.

The crystals are separated and washed with refined 70% isosorbide solution, obtained via line (4), in centrifuge (82) and discharged as a 70% solids cake via line (5). The mother liquor is recycled via line (6-5). Some of the mother liquor is purged via line (7) at a rate of about 480 lbs/hr and recycled back to the reaction-separation step. The rest, via line (6), is diluted with the cooling water of line (6-3) and is sprayed inside the vessel via line (6-4) to contact with the vapors. The centrifuged cake contains isosorbide crystals of greater than 99.8% purity that are substantially free from color-forming impurities. It is treated further with activated carbon to remove trace amounts of impurities, including any color-forming species. The cake is transported via line (5) at a rate of about 3285 lbs/hr to mixing vessel (83). It contains 2300 lbs/hr of isosorbide crystals. It is mixed in vessel (83) with demineralized water to prepare a solution of about 70% by weight isosorbide. The solution is discharged via line (9) and passed through one of the three refining columns (100-1, 2, 3) packed with activated carbon to obtain highly purified isosorbide solution. A portion of this solution is used via line (4) for washing the cake in the centrifuge, and the remaining 2385 lbs/hr is taken to a product tank via line (10). It contains 2300 lbs/hr isosorbide to provide the nominal 18 million lbs/year production. The overall process yield of isosorbide is 75% of theoretical.

What is claimed is:

1. An integrated process for continuous production of high purity, polymer grade dianhydro sugar alcohol, comprising the steps of:
   a) continuously feeding an aqueous solution of a sugar alcohol to a reaction vessel maintained at an elevated reaction temperature and a reduced pressure;
   b) contacting the sugar alcohol with a dehydration catalyst;
   c) evaporating most of the water from the aqueous solution;
   d) continuously dehydrating the sugar alcohol, with the evolution of water vapor, to form a reaction mass comprising dianhydro sugar alcohol, monoanhydro sugar alcohols, dimers and polymers;
   e) separating from the reaction mass most of the dianhydro sugar alcohol formed, by volatilizing It with the water vapor evolved to form a vapor stream and a byproduct stream; comprising monoanhydro sugar alcohol isomers, dimers, polymers, and the dianhydro sugar alcohols not volatilized from the reaction mass;
   f) withdrawing the vapor stream comprising dianhydro sugar alcohol and water from the reaction vessel, and partially condensing the stream under controlled temperature and pressure to recover most of the dianhydro sugar alcohol as a slurry of dianhydro sugar alcohol crystals in a mother liquor;
   g) separating the dianhydro sugar alcohol crystals from the mother liquor;
   h) withdrawing from the reaction vessel the byproduct stream, comprising monoanhydro sugar alcohol isomers, dimers, polymers, and the dianhydro sugar alcohols not volatilized from the reaction mass in (e);
   i) diluting the byproduct stream with water and allowing most of the polymers to precipitate;
   j) separating the precipitated polymers to form a solution of soluble sugar alcohol species; and
   k) recycling the solution of soluble species to the reaction vessel;

while maintaining the flows in and out of steps (a)–(k) at substantially steady rates and substantially steady-state processing conditions.

2. The process of claim 1, wherein the sugar alcohol is sorbitol and the dianhydro sugar alcohol is isosorbide.

3. The process of claim 2, wherein the sorbitol is an aqueous solution of about 40 weight % to 70 weight % concentration.

4. The process of claim 1, wherein the dehydration catalyst is sulfuric acid and its concentration in the reaction mass is about 0.25 weight % to 2.5 weight %.

5. The process of claim 1, wherein the evaporation and dehydration steps (c) and (d) are conducted at a temperature of 110° C. to 180° C.

6. The process of claim 1, wherein the reaction vessel is maintained at a pressure of 10 to 50 mm Hg.

7. The process of claim 1, wherein the reaction vessel is a multistage reaction vessel.

8. The process of claim 1, wherein the hold up time of the reaction mass in the vessel is 1 to 5 hours.

9. The process of claim 1, wherein the purity of vapor stream is increased within the vessel by contacting the vapor stream with a liquid stream of dianhydro sugar alcohols in a low pressure-drop vapor-liquid contacting device, wherein the liquid stream may be generated by cooling the vapor stream within the vessel or by injection of dianhydro sugar alcohols into the vessel.

10. The process of claim 1, wherein the vapor stream withdrawn from the reaction vessel is partially condensed in a low pressure-drop, direct contact spray condenser.

11. A process for the preparation, recovery and purification of dianhydro sugar alcohol, comprising:
   a) continuously feeding an aqueous solution of a sugar alcohol to a reaction vessel maintained at an elevated reaction temperature and a reduced pressure;
   b) contacting the sugar alcohol with a dehydration catalyst;
   c) evaporating most of the water from the aqueous solution;
   d) continuously dehydrating the sugar alcohol, with the evolution of water vapor, to form a reaction mass comprising dianhydro sugar alcohol, monoanhydro sugar alcohols, dimers and polymers;
   e) separating from the reaction mass most of the dianhydro sugar alcohol formed, by volatilizing it with the water vapor evolved to form a vapor stream and a byproduct stream;
   f) introducing the vapor stream into a condensation-crystallization vessel maintained at a controlled pressure and a controlled temperature;
   g) partially condensing the vapor stream, under controlled pressure and temperature, to recover most of the dianhydro sugar alcohol as a slurry of high purity crystals in a supersaturated solution;
   h) removing the uncondensed vapors, comprising mostly water, from the crystallization vessel;
   i) withdrawing the dianhydro sugar alcohol slurry from the crystallization vessel;
   j) separating the dianhydro sugar alcohol crystals from the mother liquor in the slurry;
   k) withdrawing from the reaction vessel the byproduct stream, comprising monoanhydro sugar alcohol isomers, dimers, polymers, and the dianhydro sugar alcohols not volatilized from the reaction mass in (b);
   a) diluting the byproduct stream with water and allowing most of the polymers to precipitate;
   b) separating the precipitated polymers to form a solution of soluble sugar alcohol species; and
   c) recycling the solution of soluble species to the reaction vessel; wherein steps (a) through (n) are conducted substantially continuously.

12. The process of claim 11, wherein the rates of introducing the vapor stream, removing the uncondensed vapors and withdrawing the slurry are coordinated to maintain a substantially steady level in the vessel.

13. The process of claim 11, wherein the condensation is conducted by directly contacting the vapor stream with the slurry in the vessel, maintained at a controlled temperature.

14. The process of claim 11, wherein all or a part of the condensation is conducted by directly contacting the vapor stream with a spray of recycled mother liquor.

15. The process of claim 11, wherein a stream of water is introduced into the vessel to remove the heat of condensation and crystallization.

16. The process of claim 11, wherein the partial condensation is conducted at a controlled temperature below the melting point of the dianhydro sugar alcohol.

17. The process of claim 11, wherein the partial condensation is conducted at a controlled reduced pressure of about 5 to 30 mm Hg.

18. The process of claim 1, wherein the amount of water used for precipitating the polymer is 1 to 4 pounds per pound of byproducts.

19. The process of claim 1, further comprising additional purification of the separated dianhydro sugar alcohol crystals.

20. An integrated process for continuous production of high purity, polymer grade dianhydro sugar alcohols comprising the steps of
   a. continuously dehydrating, with evolution of water vapor, an aqueous solution of a sugar alcohol, in the presence of a dehydration catalysts in a reaction vessel maintained at an elevated reaction temperature and under reduced pressure, and simultaneously separating from the reaction mass most of the dianhydro sugar alcohol formed, by volatilizing it with the water vapor evolved to form a vapor stream and a high bolting byproduct stream;
   b. withdrawing the vapor stream of (a), comprising mostly the dianhydro sugar alcohol product and water vapor, from the reaction vessel and partially condensing the stream by contacting it under controlled temperature and pressure with a glycol used in polyester production to recover most of the dianhydro sugar alcohol as a slurry of higher purity crystals in a glycol mother liquor;
   c. separating the dianhydro sugar alcohol crystals formed in (b) from the mother liquor;
   d. withdrawing the high boiling byproduct stream, comprising mostly monoanhydro sugar alcohol isomers, dimers, and polymers produced from the species present in the reaction mass, and dianhydro sugar alcohol not volatilized from the reaction mass in (a);
   e. diluting the byproducts stream from (d) with water in amount sufficient to precipitate the polymers; and
   f. separating the polymers precipitated in (e) and recycling the remaining byproduct solution to the reaction vessel, wherein the flows in and out of steps (a)–(f) are maintained at substantially steady rates and coordinated to maintain substantially steady processing conditions.

* * * * *